United States Patent [19]
Faul et al.

[11] Patent Number: 5,721,272
[45] Date of Patent: Feb. 24, 1998

[54] INTERMEDIATES AND THEIR USE TO PREPARE N,N'-BRIDGED BISINDOLYLMALEIMIDES

[75] Inventors: Margaret Mary Faul, Zionsville; Christine Ann Krumrich, Indianapolis; Leonard Larry Winneroski, Jr., Greenwood, all of Ind.

[73] Assignee: Eli Lilly and Company, Indianapolis, Ind.

[21] Appl. No.: 749,608

[22] Filed: Nov. 18, 1996

[51] Int. Cl.⁶ .................. A61K 31/35; C07D 498/22
[52] U.S. Cl. ............................ 514/450; 540/469
[58] Field of Search ..................... 514/450; 540/469

[56] References Cited

U.S. PATENT DOCUMENTS 5,541,347  7/1996  Faul et al. ..................... 552/105

FOREIGN PATENT DOCUMENTS 0 657 458  6/1995  European Pat. Off. .

Primary Examiner—Peter O'Sullivan
Attorney, Agent, or Firm—Steven P. Caltrider; David E. Boone

[57] ABSTRACT

This invention provides compounds of the formula:

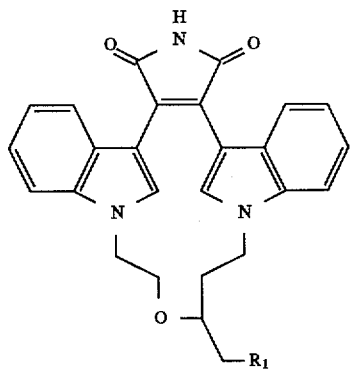

The invention further provides the use of this compound to prepare N,N'-bridged bisindolylmaleimides. Furthermore, the invention provides pharmaceutical formulations and the methods of use for inhibiting Protein Kinase C in mammals.

19 Claims, No Drawings

INTERMEDIATES AND THEIR USE TO PREPARE N,N'-BRIDGED BISINDOLYLMALEIMIDES

BACKGROUND OF THE INVENTION

The ubiquitous nature of the protein kinase C isozymes and their important roles in physiology provide incentives to produce highly selective PKC inhibitors. Given the evidence demonstrating linkage of certain isozymes to disease states, it is reasonable to assume that inhibitory compounds that are selective to one or two protein kinase C isozymes relative to the other PKC isozymes and other protein kinases are superior therapeutic agents. Such compounds demonstrate greater efficacy and lower toxicity by virtue of their specificity.

A class of PKC isozyme selective N,N'-bridged bisindolylmaleimides have been disclosed in Heath et al., 08/413735, published on Jun. 14, 1995 as EP 0 657 458. A preferred compound in this N,N'-bridged series includes a compound of the Formula I:

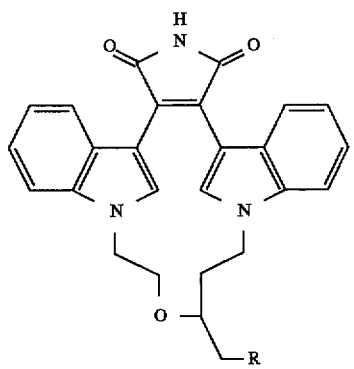

(I)

wherein R is an amino, alkylamino, or dialkylamino. Heath et al. exemplify a number of these amino substituted N,N'-bridged bisindolylmaleimides as being prepared as follows:

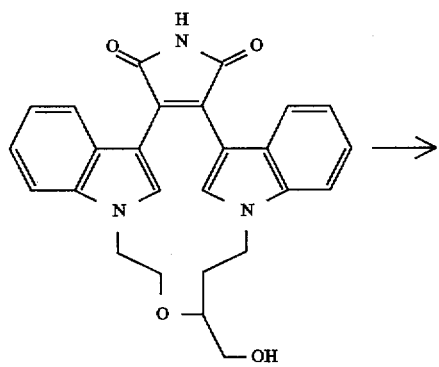

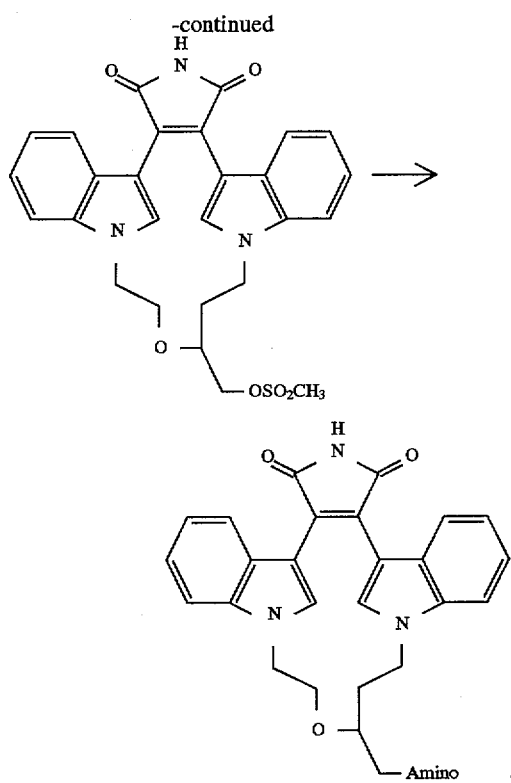

Unfortunately, the O-mesylate functionality used to prepare amino substituted N,N'-bridged bisindolylmalimides has been found to be toxic and an undesired impurity in the preparation of amino substituted N,N'-bridged bisindolylmaleimides. Expensive purification techniques must be employed to ensure that the O-mesylate intermediate is removed from the final product. Thus, there remains a need for an efficient process of preparing N,N'-bridged bisindolylmaleimides.

The present invention provides a key intermediate in the synthesis of amino substituted N,N'-bridged bisindolylmaleimides. This novel intermediate is readily converted to an amino substituted N,N'-bridged bisindolylmaleimides without passing through the OMesylate intermediate. The intermediate is also dramatically more reactive. The intermediate is preferably used to prepare amino substituted N,N'-bridged bisindolylmaleimides at lower temperatures and in a shorter reaction time resulting in a higher yield with fewer by-products. Thus, the intermediate is useful in preparing N,N'-bridged bisindolylmaleimides in high yield without undesired toxic impurities.

In addition, the claimed compounds are useful as isozyme selective PKC inhibitors. As such, the compounds are useful in treating conditions associated with diabetes mellitus and its complications, ischemia, inflammation, central nervous system disorders, cardiovascular disease, dermatological disease and cancer.

SUMMARY OF THE INVENTION

The present invention provides a compound of the Formula II:

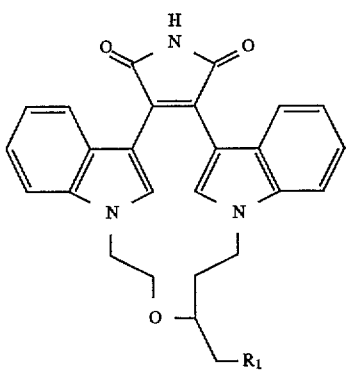

(II)

wherein R₁ is Br, I, or O-tosyl.

The present invention further provides a pharmaceutical formulation comprising a compound of Formula II and one or more pharmaceutically acceptable carriers, diluents or excipients.

One further aspect of the invention is a process of using the compound of Formula II to prepare amino substituted N,N'-bridged bisindolylmaleimides of the Formula I, which comprises reacting a compound of the Formula II with an amine in a non-reactive, polar solvent.

DETAILED DESCRIPTION AND PREFERRED EMBODIMENTS

For purposes of the present invention, as disclosed and claimed herein, the following terms and abbreviations are defined as follows.

The term "$C_1$–$C_4$ alkyl" represents a cyclo, straight or branched chain alkyl group having from one to four carbon atoms such as methyl, ethyl, n-propyl, isopropyl, cyclopropyl, n-butyl, isobutyl, sec-butyl, t-butyl and the like.

The term "aryl" represents a substituted or unsubstituted benzyl, phenyl, or naphthyl.

The term "amine" as used herein refers to —N(CF₃)CH₃), —NH(CF₃), or —NR₃R₄ wherein R₃ and R₄ are independently hydrogen, $C_1$–$C_4$ alkyl, phenyl, benzyl, or combine to the nitrogen to which they are bonded to form a saturated or unsaturated 5 or 6 member ring.

As noted above, the invention provides a compound of the Formula II:

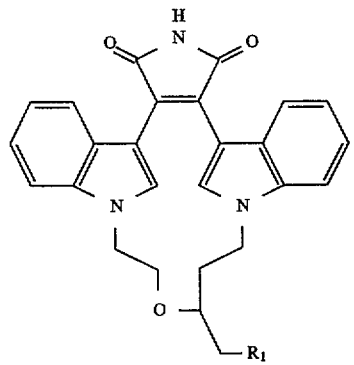

(II)

wherein R₁ is Br, I, or O-tosyl.

It is recognized that various stereoisomeric forms of the compounds of Formula II may exist. The preferred compounds of the present invention are of the Formula IIa and IIb:

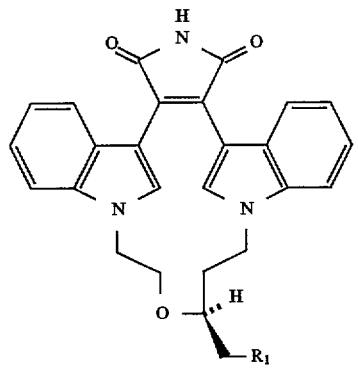

(IIa)

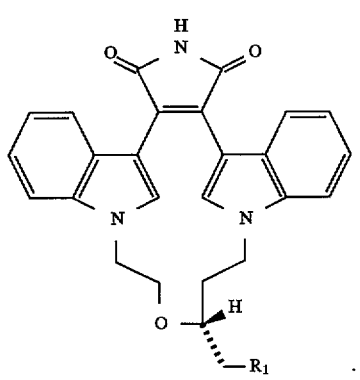

(IIb)

However, racemates and individual enantiomers and mixtures thereof form part of the present invention.

The compounds of the present invention are most readily prepared from a compound of the formula:

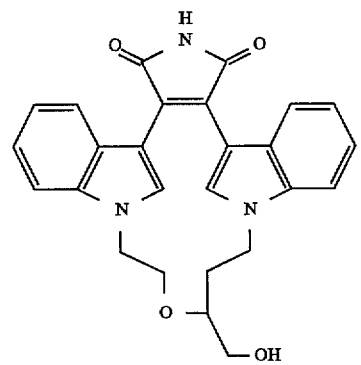

(III)

This hydroxy substituted N,N'-bridged bisindolylmaleimide, compound III, is prepared by techniques described in Heath et al., 08/413735, published on Jun. 14, 1995 as EP 0 857 458, herein incorporated by reference.

The claimed compounds are prepared as follows:

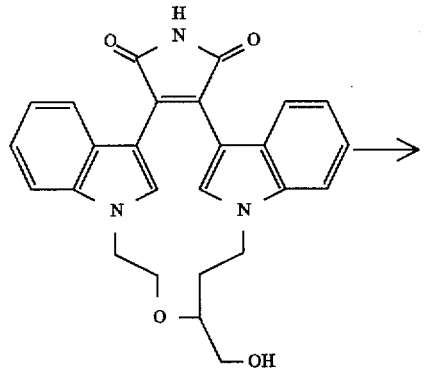

(III)

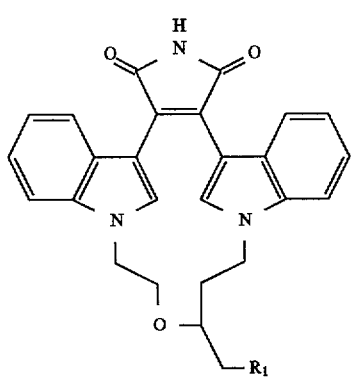

(II)

$R_1$ is the same as previously defined. Preferably, $R_1$ is Br or I, most preferably $R_1$ is Br. The claimed tosylate (p-toluenesulfonyl) compounds are prepared by reacting the alcohol with p-toluenesulfonic anhydride in the presence of a base such as pyridine in THF, ether, methylene chloride, or other non-reactive organic solvent. The reaction is generally carried out under nitrogen from room temperature to the reflux temperature of the reaction mixture.

The claimed halides are prepared by reacting the alcohol with a bromide or iodide source. The bromide or iodide source can be a number of reagents appreciated in the art including: HI, HBr, LiBr, $CaBr_2$, $PBr_3$, $R_5PBr_2$, N-bromosuccinimide, $CBr_4$, allyl-Br, Benzyl-Br, $SOBr_2$; wherein $R_5$ is phenyl, phenyloxy, alkyl or aryl. One skilled in the art would recognize that various activating agents such as 1,1'- carbonyldiimidazole may be added to the reaction. The conversion of a hydroxy (III) to a halide (II) can be carried out by techniques appreciated in the art and disclosed in Richard C. Larock, A GUIDE TO FUNCTIONAL GROUP PREPARATIONS, VCH Publishers, p. 356–63 (1989), herein incorporated by reference. Preferred conditions include the bromide or iodide in the presence of a phosphorous halide reagent such as $PX_3$, $(phenyl)_3PX_2$, or $(phenoxy)_3PX_2$ wherein X is bromo or iodo. The reaction is suitably carried out in THF, acetonitrile, methylene chloride, or other non-reactive solvents appreciated in the art. DMF or other solvents are also operative due to formation of an Vilsmeier-type reagent as described in Barluenga J. *Synthesis* p. 426 (1985) and Hodosi G, *Carbohydrate Research* 230: 327–42 (1992).

Compounds of the Formula II are converted to the amino substituted N,N'-bridged bisindolylmaleimides of the Formula IV, as follows:

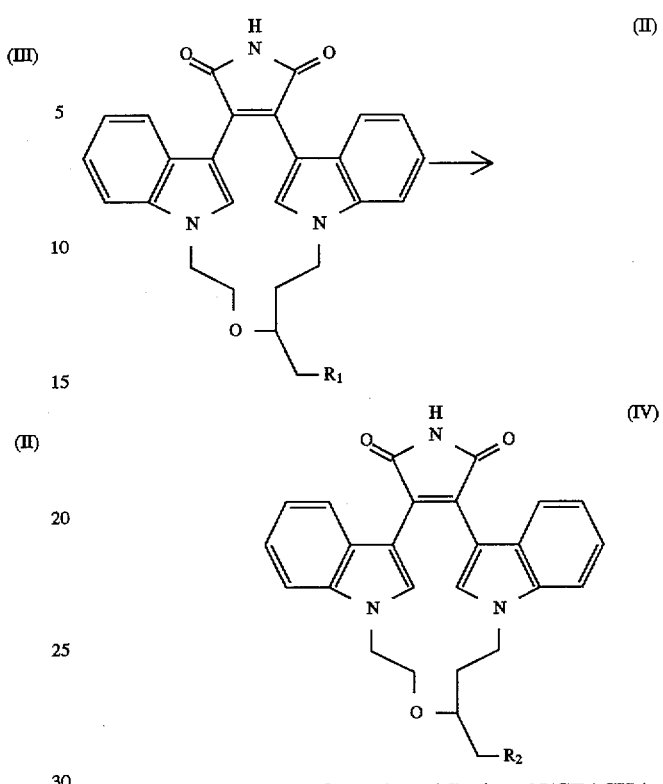

wherein $R_1$ is Br, I, or O-tosyl; and $R_2$ is —$N(CF_3)CH_3$), —$NH(CF_3)$, or —$NR_3R_4$ wherein $R_3$ and $R_4$ are independently hydrogen, $C_1$–$C_4$ alkyl, phenyl, benzyl, or combine to the nitrogen to which they are bonded to form a saturated or unsaturated 5 or 6 member ring. Preferably, $R_2$ in $N(CH_3)$.

The process of using Compound II to form Compound IV, comprises reacting a Compound II with an amine of the formula: $HN(CF_3)CH_3$), $HNH(CF_3)$, or $HNR_3R_4$ wherein $R_3$ and $R_4$ are independently hydrogen, $C_1$–$C_4$ alkyl, phenyl, benzyl, or combine to the nitrogen to which they are bonded to form a saturated or unsaturated 5 or 6 member ring, in a non-reactive, polar aprotic solvent. The reaction is preferably carried out in a solution of DMF, THF:water, or dimetylacetamide at temperatures ranging from 0° C. to the reflux temperature of the reaction mixture. The reaction generally is complete in about 1 to 20 hours. Preferably, the reaction is carried out at room temperature to 50° C. Compound IV may be purified from the reaction mixture using standard techniques but is preferably crystallized directly from the reaction mixture.

Most unexpectedly, the use of the claimed intermediate to prepare a amino-substituted N,N'-bisindolylmaleimide results in a higher yield and avoids toxic impurities. The claimed intermediate is surprisingly more reactive than the known mesylate intermediate. The reactivity of various leaving groups to $HN(CH_3)_2$ is presented in Table I. The relative reactivity predicted in the art is described in CAREY AND SUNDBERG, Part A, 3rd Edition, page 291 (1990).

TABLE I

| Reaction rates with $HN(CH_3)_2$ | |
|---|---|
| Group | $K_{rel}$ (Rate of reaction of leaving groups with $HN(CH_3)_2$) |
| p-toluenesulfonate | $2.2 \times 10^{-2}$ |
| MsO⁻ | $5.5 \times 10^{-3}$ |

TABLE I-continued

Reaction rates with $HN(CH_3)_2$

| Group | $K_{rel}$ (Rate of reaction of leaving groups with $HN(CH_3)_2$) |
| --- | --- |
| Cl⁻ | $9.8 \times 10^{-4}$ |
| I⁻ | $2.0 \times 10^{-1}$ |
| Br⁻ | $2.2 \times 10^{-2}$ |

The data in Table I demonstrate that the tosyl, bromide and iodide are unexpectedly reactive—particularly the bromide and iodide which are from 8× to 36× more reactive than the known mesylate intermediate. This enhanced reactivity relative to MsO was also observed with $H_2NCH_3$, $H_2N$(benzyl). The increase in reactivity results in a lower temperature reaction that is complete in a shorter period of time. The use of the claimed intermediate also results in fewer impurities in the product. Using the known O-Mesyl intermediate, the reaction to produce an amino substituted N,N'-bisindolylmaleimide results in an impurity level from 15 to 30% due to by-products formed from reaction at the maleimide carbonyl group. Using the claimed intermediate, the impurity level is less than 5%, a substantial improvement.

As previously stated, the O-mesylate functionality used to prepare amino substituted N,N' bridged bisindolylmalimides has been found to be toxic and an undesired impurity in the preparation of amino substituted N,N'-bridged bisindolylmaleimides. Expensive purification techniques must be employed to ensure that the O-mesylate intermediate is removed from the final product. Therefore, an additional advantage of the present intermediates and process for preparing amino substituted N,N' bridged bisindolylmalimides using the claimed intermediates is avoiding difficult purification steps to remove toxic impurities.

The preferred compounds prepared using the claimed intermediates are the following: (S)-13-[(Dimethylamino)methyl]-10,11,14,15-tetrahydro-4,9:16, 21-dimetheno-1H,13H-dibenzo[E,K]pyrrolo-[3,4-H][1,4,13]oxadiaza-cyclohexadecine-1,3(2H)-dione, particularly as the mesylate salt; (S)-13-[(Monomethylamino)methyl]-10,11,14,15-tetrahydro-4,9:16,21-dimetheno-1H,13H-dibenzo[E,K]pyrrolo-[3,4-H][1,4,13]oxadiaza-cyclohexadecine-1,3(2H)-dione; (S)-13-[(pyrrolidino)methyl]-10,11,14,15-tetrahydro-4,9:16,21-dimetheno-1H,13H-dibenzo[E,K]pyrrolo-[3,4-H][1,4,13]oxadiaza-cyclohexadecine-1,3(2H)-dione monohydrochloride; and (S)-13-[benzylaminomethyl]-10,11,14,15-tetrahydro-4,9:16,21-dimetheno-1H,13H-dibenzo[E,K]pyrrolo-[3,4-H][1,4,13]oxadiaza-cyclohexadecine-1,3(2H)-dione.

The preferred mono-substituted amines of the Formula IV may be prepared directly from the claimed compounds. A high yielding direct method to prepare these compounds is not possible with the mesylate intermediate.

The compounds of the Formula IV are prepared as the free base and are preferably converted to a pharmaceutically acceptable salt by techniques appreciated in the art. Preferred salts include the hydrochloride and mesylate salt.

The following examples and preparations are provided merely to further illustrate the invention. The scope of the invention is not construed as merely consisting of the following examples. In the following examples and preparations, melting point, nuclear magnetic resonance spectra, mass spectra, high pressure liquid chromatography over silica gel, N,N-dimethylformamide, tetrahydrofuran, and ethyl acetate are abbreviated M.Pt., NMR, MS, HPLC, DMF, THF, and EtOAc respectively. The terms "NMR" and "MS" indicate that the spectrum was consistent with the desired structure.

PREPARATION 1

3-(2-[(methylsulfonyl)oxylethoxy]-4-triphenylmethoxy)-1-butanol methane sulfonate Trityl chloride (175.2 g, 0.616 mole) was dissolved in 500 mL of $CH_2Cl_2$ under $N_2$. Triethylamine (71.9 g, 100 mL, 0.710 mole) was added and then R,S-glycidol (50.0 g, 0.648 mole) was added, and the reaction solution was heated to a gentle reflux (42° C.) for 4 hours. The reaction was cooled to room temperature and was extracted twice with 250 mL of an aqueous saturated solution of ammonium chloride and then 250 mL of brine. The aqueous layers were back-extracted with 100 mL of $CH_2Cl_2$ and the organic layer was dried ($MgSO_4$) and evaporated in vacuo to give and trityl-glycidol as an oil that was recrystallized from ethanol to give 104.4 g (54%) of trityl-glycidol as a solid.

A 1M THF solution of vinylmagnesium bromide (50 mL, 50 mmol, 2.0 eq.) was cooled to $-20°$ C. under $N_2$ and a catalytic amount of copper iodide was added (0.24 g, 1.26 mmol, 0.05 eq). The resultant mixture was stirred at $-20°$ C. for 5 minutes and then a solution of trityl-glycidol (7.91 g, 25.0 mmol) in 40 mL of dry THF was added dropwise over 15 minutes at $-20°$ C. The reaction mixture was stirred for 3 hours at $-20°$ C. and then was allowed to warm to room temperature and stir for 15 minutes. The reaction was quenched by cooling the reaction mixture to $-30°$ C. and 125 mL of an aqueous saturated solution of ammonium chloride was slowly added. The resultant mixture was extracted with 200 mL of ethyl acetate. The organic layer wan then extracted with an aqueous solution of 0.93 g (2.50 mmol, 0.1 eq.) of ethylenediaminetetraacetic acid, disodium salt dihydrate (EDTA) in 125 mL of deionized water to remove any metals. The aqueous layers were back extracted with 50 mL of ethyl acetate and the combined organic layers were washed with 100 mL of brine, dried ($MgSO_4$) and evaporated in vacuo to give an oil that was filtered through silica (76 g) using 1.2 L of 3/1 hexanes/ethyl acetate. The filtrate was evaporated in vacuo to give 9.07 g of 1-(triphenylmethoxy)-4-penten-2-ol as a light yellow colored oil (100%).

A 60% suspension of sodium hydride in mineral oil (6.13 g, 0.153 mol, 1.5 eq.) was suspended in 175 mL of dry THF was added at room temperature. The resultant mixture was stirred at 45° C. for 1.5 hours and then 17.7 mL (0.204 mmol, 2.0 eq.) of freshly distilled allyl bromide was added via syringe. The reaction was heated to 45° C. for 1 hour. The reaction can be monitored by TLC or HPLC. The reaction mixture was cooled to 0° C. and 400 mL of an aqueous saturated solution of ammonium chloride was slowly added to quench the excess base. The resultant mixture was extracted with 800 mL of ethyl acetate and the organic layer was washed with 500 mL of water. The aqueous layers were back-extracted with 100 mL of ethyl acetate and the combined organic layers were washed with 200 mL of brine, dried ($MgSO_4$) and evaporated in vacuo to give 41.5 g (>100%) of 1,1',1"-[[[2-(2-propenyloxy)-4-pentenyl]oxy]methylidyne]tris[benzene] as a yellow oil.

1,1',1"-[[[2-(2-propenyloxy)-4-pentenyl]oxy]methylidyne]tris[benzene] (39.3 g, 0.102 mol) was dissolved in a solution of 390 mL of anhydrous methyl alcohol and 60 mL of $CH_2Cl_2$ and was cooled to $-50°$ to $-40°$ C. while bubbling $N_2$ through the viscous reaction solution. Ozone was then bubbled through the reaction mixture at $-50°$ to $-40°$ C. for 80 minutes until the reaction turned pail blue in color. The resultant reaction mixture was allowed to warm to 0° C. under $N_2$ and then a solution of sodium borohydride (23.15 g, 0.612 mole, 6 eq.) in 85 mL ethanol / 85 mL water was slowly added to quench the reaction while keeping the reaction temperature below 10° C. The reaction was stirred in an ice bath for 30 minutes and then was allowed to warm to room temperature and stir overnight. The temperature rose to 31° C. upon warming. The reaction mixture was diluted with 400 mL of an aqueous saturated solution of ammonium chloride and was extracted with 800 mL of ethyl acetate. The organic layer was washed with 400 mL of water and the aqueous layers were back-extracted with 150 mL of ethyl acetate. The combined organic layer was washed with 200 mL of brine and was dried ($MgSO_4$) and evaporated in vacuo to give a cloudy oil. This oil was recrystallized from 2/1 hexanes/ethyl acetate in 3 crops to give 28.9 g of 3-(2-hydroxyethoxy)-4-(triphenylmethoxy)-1-butanol (72%).

3-(2-hydroxyethoxy)-4-(triphenylmethoxy)-1-butanol (14.0 g, 35.7 mmol) was dissolved in 140 mL of $CH_2Cl_2$, was cooled to 0° C. under $N_2$, and triethylamine (10.8 g, 14.9 mL, 0.107 mol. 3.0 eq.) was added. Methanesulfonyl chloride (11.0 g, 7.46 mL, 96.4 mmol, 2.7 eq.) was then added dropwise at <5° C. The resultant reaction mixture was diluted with additional $CH_2Cl_2$ (300 mL) and was washed with 200 mL of water and 200 mL of an aqueous saturated solution of ammonium chloride. The aqueous layers were back-extracted with 50 mL of $CH_2Cl_2$ and the combined organic layer was washed with 100 mL of brine and was dried ($MgSO_4$) and evaporated in vacuo to give 18.4 g (94%) of 3-(2-[(methylsulfonyl)oxy]ethoxy]-4-triphenylmethoxy)-1-butanol methane sulfonate as a white solid.

PREPARATION 2

(S)-Trityl Glycidol

Trityl chloride (2866 g, 10.3 mole) was dissolved in 7 L of $CH_2Cl_2$ under $N_2$. Triethylamine (1189 g, 1638 mL, 11.8 mole) was added, and then (R)-(+)-glycidol (795.0 g, 10.6 mole) was added using 1 L of $CH_2Cl_2$ as a rinse. The reaction solution was heated to a gentle reflux (42° C.) for 3-4 hours. The reaction was cooled to room temperature and then 3 L of brine was added. The organic layer was dried (600 g $Na_2SO_4$) and evaporated in vacuo to give the titled compound as an oil that was recrystallized from ethanol to give 2354 g (70%) of the titled compound as a solid.

PREPARATION 3

(S)-3-[2-[(methylsulfonyl)oxy]ethoxy]-4-(triphenylmethoxy)-1-butanol methanesulfonate A 1M THF solution of vinylmagnesium bromide (5.76 L, 5.76 mole, 1.96 eq.) was cooled to −20° C. under $N_2$ and a catalytic amount of copper iodide was added (28.2 g, 0.148 mole, 0.05 eq.). The resultant mixture was stirred at −20° C. for 5 minutes, and then a solution of (S)-Trityl-glycidol (929.0 g, 2.94 mole) in 3.2 L of dry THF was added dropwise over 1.5 hours at −20° C. The reaction mixture was stirred for 1 hour at −20° C. The reaction was quenched by cooling the reaction mixture to −30° C. and 5 L of an aqueous saturated solution of ammonium chloride was slowly added. The organic layer was then extracted twice with 1 L a 10% wt./volume solution of ethylenediaminetetraacetic acid, disodium salt dihydrate (EDTA) to remove any metals. The organic layer was washed with 2 L of brine, dried ($MgSO_4$) and evaporated in vacuo to give 1061 g (96%) of (S)-1-0-triphenylmethyl-4-hydroxypentanol as an oil.

A 60% suspension of sodium hydride in mineral oil (268.9 g, 6.72 mole, 1.5 eq.) was suspended in 2.8 L of dry THF under $N_2$ and a solution (S)-1-0-triphenylmethyl-4-hydroxypentanol (1543 g, 4.48 mole) in 5.6 L of dry THF was added at room temperature. The resultant mixture was stirred at room temperature for 1.5 hours and then 770 mL (8.89 mole, 2.0 eq.) of freshly distilled allyl bromide was added over 20 minutes. The reaction was heated to 45° C. for 1-2 hours. The reaction mixture was cooled to 15°-20° C. and 2 L of an aqueous saturated solution of ammonium chloride was slowly added to quench the excess base. The resultant mixture was diluted with 1 L of ethyl acetate and 1 L of water and the organic layer was isolated. The aqueous layer was back-extracted with 500 mL of ethyl acetate and the combined organic layers were dried ($MgSO_4$) and evaporated in vacuo to give 1867 g (98%) of (S)-1,1',1"-[[ [2-(2-propenyloxy)-4-pentenyl]oxy]methylidyne]tris [benzene] as a yellow oil.

(S)-1,1',1"-[[[2-(2-propenyloxy)-4-pentenyl]oxy] methylidyne]tris[benzene] (1281 g, 3.33 mole) was dissolved in a solution of 4 L of anhydrous methyl alcohol and 3.6 L of $CH_2Cl_2$ and was cooled to −50° to −40° C. while bubbling $N_2$ through the viscous reaction solution. Sudan III indicator was added to the reaction and ozone was bubbled through the reaction mixture at −50° to −35° C. for 13 hours until the reaction turned from a peach color to a light green/yellow color. The resultant reaction mixture was allowed to warm to 0° C. under $N_2$ and was then slowly added over 40 minutes to a solution of sodium borohydride (754 g, 19.9 mole, 6 eq.) in 2.5 L ethanol / 2.5 L water while keeping the reaction temperature below 30° C. The reaction was then allowed to stir at room temperature overnight. The reaction can be monitored by HPLC. The reaction mixture was cooled to 10°-15° C. and was slowly added to 4 L of an aqueous saturated solution of ammonium chloride at <20° C. The quenched reaction mixture was then filtered and the solids washed with 3 L of $CH_2Cl_2$. The organic layer was isolated and was washed with 3 L of an aqueous saturated solution of ammonium chloride and the aqueous layers were back-extracted with 1 L of $CH_2Cl_2$. The combined organic layer was dried ($MgSO_4$) and evaporated in vacuo to give a 1361 g (>100%) of (S)-3-(2-hydroxyethoxy)-4-(tripenylmethoxy)-1-butanol as a oil.

(S)-3-(2-hydroxyethoxy)-4-(tripenylmethoxy)-1-butanol (500 g, 1.27 mole) was dissolved in 4.8 L of $CH_2Cl_2$, was cooled to 0° C. under $N_2$, and triethylamine (386.4 g, 532 mL, 3.81 mole, 3.0 eq.) was added. Methanesulfonyl chloride (396.3 g, 268 mL, 3.46 mole, 2.7 eq.) was then added dropwise over 30 minutes at <5° C. The resultant reaction mixture was stirred at 0° to 5° C. for 1-2 hours and was monitored by HPLC. The reaction mixture was diluted with additional $CH_2Cl_2$ and was washed twice with 2 L of water and 2 L of an aqueous saturated solution of ammonium chloride. The aqueous layers were back-extracted with 1 L of $CH_2Cl_2$ and the combined organic layer was dried ($MgSO_4$) and evaporated in vacuo to give a crude solid that was recrystallized from 1/1 heptane/ethyl acetate to give 615 g (88%) of (S)-3-[2-[(methylsulfonyl)oxy]ethoxy]-4-(triphenylmethoxy)-1-butanol methane sulfonate in three crops as a solid. NMR. MS.

PREPARATION 4

(S)-10,11,14,15-tetrahydro-13-(hydroxymethyl)-4,9:16,21-dimetheno-1H, 13H-dibenzo[E,K]pyrrolo[3,4-H][1,4,13] oxadiazacyclohexadecine-1,3(2H)-dione 2,3-Bis- (1H-indol-3-yl)-N-methylmaleimide (114.7 g, 0.336 mole ) and (S)-3-[2-[(methylsulfonyl) oxy]ethoxy]-4-

(triphenylmethoxy)-1-butanol methane sulfonate (220.0 g, 0.401 mole, 1.2 eq.) were dissolved in 4.3 L of DMF. This solution of reagents was then added slowly over 70 hours (at approximately 1 mL/min) to a 50° C. slurry of cesium carbonate (437.8 g, 1.34 mole, 4.0 eq.) in 7 L of DMF. After 70–72 hours the reaction was cooled and filtered, and the DMF was removed in vacuo to give a residue that was dissolved in 4.6 L of $CH_2Cl_2$. The organic layer was extracted with 1.15 L of aqueous 1N HCl and then with 4.6 L of brine. The combined aqueous layers were back-extracted with 1.1 L of $CH_2Cl_2$. The combined organic layer was dried ($Na_2SO_4$) and filtered. Most of the solvent was removed in vacuo, and the resultant solution was filtered through 2 Kg of silica gel using 4–5 gallons of additional $CH_2Cl_2$ to remove baseline material. The solvent was removed in vacuo and the resultant purple colored solid triturated in 7 volumes of acetonitrile (based on weight of crude (S)-10,11,14,15-tetrahydro-2-methyl-13-[(triphenylmethoxy) methyl]-4,9:16,21-dimetheno-1H, 13H-dibenzo[E,K]pyrrolo[3,4-H][1,4,13]oxadiazacyclohexadecine-1,3(2H)-dione) to give 150.2 g (57%) of (S)-10,11,14,15-tetrahydro-2-methyl-13-[(triphenylmethoxy) methyl]-4,9:16,21-dimetheno-1H, 13H-dibenzo [E, K]pyrrolo [3,4-H][1,4,13]oxadiazacyclohexadecine-1,3 (2H) -dione after drying (89% pure by HPLC vs. standard).

(S) -10,11,14,15-tetrahydro-2-methyl-13-[(triphenylmethoxy) methyl ]-4,9:16,21 -dimetheno- 1H, 13H-dibenzo[E,K]pyrrolo[3,4-H][1,4,13] oxadiazacyclohexadecine-1,3(2H)-dione (32.7 g, 46.9 mmol) was suspended in 1.6 L of ethanol and 1.6 L of aqueous 10 N KOH. The resultant mixture was heated to a gentle reflux (78° C.) for 19 hours. Most of the solids dissolved upon reaching reflux. The reaction solution was cooled to 10° to 15° C. and aqueous 10N HCl (1.2 L) was slowly added at <15° C. to adjust the acidity to pH=1. A red slurry developed upon acidification. The reaction mixture was diluted with 500 mL of $CH_2Cl_2$ and was stirred for 20 minutes and filtered to remove most of the salts. The salts were washed with additional $CH_2Cl_2$ (1.5 L), and the filtrate was extracted twice with 1 L of water. The combined aqueous layers were back-extracted with 1 L of $CH_2Cl_2$, and the organic layer was dried ($MgSO_4$). The solvent was removed in vacuo to give 36.0 g (>100%) (S)-10,11,14,15-tetrahydro-13-[(triphenylmethoxy)methyl]-4,9:16,21-dimetheno-13H-dibenzo[E,K]furo[3,4-H][1,4,13]oxadiazacyclohexadecine-1,3-dione as a purple solid (80% pure by HPLC area).

(S)-10,11,14,15-tetrahydro-13-[(triphenylmethoxy) methyl]-4,9:16,21-dimetheno-13H-dibenzo[E,K]furo[3,4-H][1,4,13]oxadiazacyclohexadecine-1,3-dione (36.0 g, assume 46.9 mmol) was dissolved in 320 mL of dry DMF under $N_2$ and was treated with a pre-mixed solution of 1,1,1,3,3,3-hexamethyldisilazane (99 mL, 75.7 g, 0.469 mol, 10 eq.) and methanol (9.5 mL, 7.51 g, 0.235 mol. 5 eq.). The resultant solution was heated at 45° C. for 7 hours. The reaction can be monitored by HPLC. Most of the DMF was removed in vacuo, and the resultant residue was extracted into 200 mL of ethyl acetate and washed with 200 mL of water and twice with 100 mL of an aqueous 5% LiCl solution. The aqueous layers were back-extracted with 100 mL of ethyl acetate. The combined organic layer was washed with 200 mL of a saturated aqueous solution of ammonium chloride. The combined organic layer was dried ($MgSO_4$) and evaporated in vacuo to give 35.9 g (>100%) of the crude (S)-10,11,14,15-tetrahydro-13-[(triphenylmethoxy)methyl]-4,9:16,21-dimetheno-1H; 13H-dibenzo[E,K]pyrrolo[3,4-H][1,4,13] oxadiazacyclohexadecine-1,3(2H)-dione as a purple solid.

(S)-10,11,14,15-tetrahydro-13-[(triphenylmethoxy) methyl]-4,9:16,21-dimeth-eno-1H; 13H-dibenzo[E,K] pyrrolo[3,4-H][1,4,13]oxadiazacyclohexadecine-1,3(2H)-dione (34.0, assume 46.8 mmol) was dissolved in 350 mL of $CH_2Cl_2$ and was cooled to −25° C. under $N_2$. Anhydrous HCl gas was bubbled into the reaction solution for approximately 1–2 minutes at <0° C. The resultant slurry was allowed to warm to room temperature and stir for 1 hour. The reaction can be monitored by HPLC. The slurry was filtered and the solids were washed with 200 mL of $CH_2Cl_2$. The solid was dried in a vacuum oven at 50° C. to give 18.6 g (90%) (S)-10,11,14,15-tetrahydro-13-(hydroxymethyl)-4, 9:16,21-dimetheno-1H,13H-dibenzo[E,K]pyrrolo[3,4-H][1, 4,13]oxadiazacyclohexadecine-1,3(2H)-dione as a purple solid (93% pure by HPLC area).

EXAMPLE 1

(S)-10,11,14,15-tetrahydro-13-[bromo(methyl)]-4,9:16,21-dimetheno-1H,13H-dibenzo[E,K]pyrrolo[3,4-H][1,4,13] oxadiazacyclohexadecine-1,3(2H)-dione Bromine (2.0 equiv) and pyridine (0.1 equiv) were charged into methylene chloride (10 vols), and the solution cooled to −5° C. The bromine was titrated with triphenylphosphite (2.0 equiv). The solution turned from yellow to clear when all the bromine was consumed. To a second reactor was charged (S)-10,11,14,15-tetrahydro-13-[hydroxy(methyl)]-4,9:16,21-dimetheno-1H,13H-dibenzo [E,K]pyrrolo[3,4-H][1,4,13]oxa-diazacyclohexadecine-1,3 (2H)-dione (1.0 equiv) in methylene chloride (10 vols). The slurry was cooled to −5° C. The triphenylphosphite dibromide solution was then added to the pyrrolodione slurry, and the reaction allowed to warm to room temperature and stir for 12–16 hrs until the complete (<0.4% Compound III by HPLC). The slurry was concentrated under vacuum at room temperature over 2 hrs, then quenched with 1 volume of deionized water and stirred for 15 min. Toluene (40 vols) was charged into the reaction slurry to precipitate the product. After stirring at 10° C. for 1 hr the product was isolated by filtration and washed twice toluene (5 vols), deionized water (5 vols) and a final rinse with 5 volumes of toluene. The titled bromide was dried in a vacuum dryer at 521 50° C. Yields 85–90% (impurities 1–2%).

To further reduce the level of impurities, the product is reslurried in a solvent system such as acetone: water, methanol:water, isopropanol:water, or ethyl acetate. Preferably the product is reslurried in THF:water at a ratio from 1:1 to 5:1 (THF:water).

EXAMPLE 2

(S)-13-[(Dimethylamino)methyl]-10,11,14,15-tetrahydro-4, 9:16,21-dimetheno-1H,13H-dibenzo[E,K]pyrrolo-[3,4-H] [1,4,13]oxa-diaza-cyclohexadecine-1,3(2H/-dione To a solution of (S)-10,11,14,15-tetrahydro-13-[bromo (methyl)]-4,9:16,21-dimetheno-1H,13H-dibenzo[E,K] pyrrolo[3,4-H][1,4,13]oxadiaza-cyclohexadecine-1,3(2H)-dione (1.0 equiv) in N,N-dimethylformamide (17 vol.) was added dimethylamine (10.73 Kg, 12 equiv). The reaction vessel was sealed and heated at 45° C. for 9 hr. The reaction was then cooled to room temperature and stirred for 12–16 hr. NaOH (12N, 1.1 equiv) was added to the reaction to form the freebase. The solution stirred for an additional 2 hr. After removal of the N,N-dimethylformamide in vacuo to 5–7 vols, MeOH (30 vols) at 60° C, added to the reaction also at 60 ° C. over 1 hr. The reaction was then cooled to room temperature and stirred overnight, then cooled further to 0°–10° C. The product was isolated by filtration and washed with MeOH (3 vols). The material was dried in a vacuum dryer at 50° C. to a constant weight. Yields 85–92%. Other solvents which have been employed in this reaction are THF/water and dimethylacetamide, due to the low solubility of starting material and products the reaction should be carried out in a polar aprotic solvent. Other bases have been examined (see below) to free the HBr salt in situ but the most effective bases were 6N NaOH, 12N NaOH and $K_2CO_3$.

EXAMPLE 3

(S)-10,11,14,15-tetrahydro-13-[iodo(methyl)]-4,9:16,21-dimetheno-1H,13H-dibenzo[E,K]pyrrolo[3,4-H][1,4,13] oxa-diazacyclohexadecine-1,3(2H)-dione (S)-10,11,14,15-tetrahydro-13-[methanesulfonyloxy]-4,9:16,21-dimetheno-1H,13H-dibenzo[E,K]pyrrolo[3,4-H][1,4,13]oxa-diazacyclohexadecine-1,3(2H)-dione (1.0 g, 1.94 mmol) was taken up in 20 mL dry N,N-dimethylformamide (20 vol.). To the solution was added sodium iodide (3.0 g, 19.4 mmol, 10.0 equiv.), and the reaction was stirred and heated at 50° C. for 36 hrs. On cooling the reaction to ambient temperature the product was isolated by addition of water (50 mL, 50 vol.). The product precipitated out as a purple solid which was recrystallized from 5:1 THF:$H_2O$ to give 0.87 g (81of the titled compound.

EXAMPLE 4

(S)-10,11,14,15-tetrahydro-13-[p-toluenesulfonyloxy (methyl)]-4,9:16,21-dimetheno-1H,13H-dibenzo[E,K] pyrrolo[3,4-H][1,4,13]oxa-diazacyclohexadecine-1,3(2H)-dione (S)-10,11,14,15-tetrahydro-13-[hydroxymethyl]-4,9:16,21-dimetheno-1H,13H-dibenzo[E,K]pyrrolo[3,4-H][1,4,13] oxa-diazacyclohexadecine-1,3(2H)-dione(1.0 g, 2.27 mmol) was taken up in 20 mL dichloromethane (20 vol.). To the solution was added toluenesulfonic anhydride (2.22 g, 6.80 mmol, 3.0 equiv.) and pyridine (0.72 g, 9.08 mmol, 4.0 equiv.) and the reaction was stirred and heated to reflux at 42° C. for 2 hrs. The reaction was cooled to ambient temperature and diluted with 40 mL dichloromethane. The organic phase was washed with 50 mL 1N hydrochloric acid and 50 mL brine. The aqueous layers were back extracted with 30 mL dichloromethane and the combined organics were solvent exchanged from methylene chloride into ethanol. The product precipitated out as a purple solid and was filtered to give 1.25 g (93% yield) of the titled compound.

EXAMPLE 5

(S)-13-[(Monomethylamino)methyl]-10,11,14,15-tetrahydro-4,9:16,21-dimetheno-1H,13H-dibenzo[E,K] pyrrolo-[3,4-H][1,4,13]oxadiaza-cyclohexadecine-1,3(2H)-dione Methylamine (37.1 g, 1.19 moles, 20 eq.) was dissolved in 600 mL of N,N-dimethylacetamide keeping the temperature below 23° C. To the solution was added the compound of Example 1 (30 g, 0.0595 moles). The reaction was stirred at ambient temperature for 24 hrs in a sealed vessel. Triethylamine (8.3 mL, 0.0595 moles, 1 eq.) was added to scavenge the HBr formed in the reaction and the reaction was stirred an additional 30 minutes and then cooled to 4° C. and water (450 mL) was slowly added while keeping the reaction temperature below 25° C. A slurry developed upon the addition of water, which was stirred 1 hour and filtered using 200 mL of additional water to wash the filtered solid.

The solid was dried in a vacuum oven at 50° C. to give 25.03 g (93%) of the titled compound.

EXAMPLE 6

(S)-13-[(pyrrolidino)methyl]-10,11,14,15-tetrahydro-4,9:16,21-dimetheno-1H,13H-dibenzo[E,K]pyrrolo-[3,4-H] [1,4,13]oxadiaza-cyclohexadecine-1,3(2H)-dione monohydrochloride The compound of Example 1 (1.0 g, 1.0 equiv) was taken up in 5 mL of N,N-dimethylacetamide and pyrrolidine (1.6 mL, 10 equiv) added. The reaction was heated at 45° C. for 9 hr then cooled to room temperature. To the red slurry was added 12N NaOH (0.17 mL, 1.0 equiv) and the mixture stirred at room temp for 2 hr to afford a red solution. The solvent removed in vacuo, and the oil the diluted with methylene chloride (100 mL) and washed with saturated ammonium chloride (100 mL) and 5% LiCl solution (2×100 mL). Removal of the methylene chloride in vacuo afforded an oil, from which the titled compound precipitated as a red solid on addition of methyl t-butylether. The solid was isolated by filtration and dried in a vacuum oven at 50° C. overnight to afford 0.8 g (81%) product.

EXAMPLE 7

(S)-13-[benzylaminomethyl]-10,11,14,15-tetrahydro-4,9:16,21-dimetheno-1H,13H-dibenzo[E,K]pyrrolo-[3,4-H] [1,4,13]oxadiaza-cyclohexadecine-1,3(2H)-dione The compound of Example 1 was taken up in 20 vol. of N,N-dimethylacetamide and benzylamine (6.0 eq.) was added in one portion. The reaction was stirred and heated at 80° C. for 24 hrs. in a sealed vessel. The reaction was cooled to ambient temperature and triethylamine (1 eq.) was added to scavenge the HBr and the reaction was stirred for 30 additional minutes. Ethyl acetate was added and the organic layer was washed with a saturated solution of sodium chloride. The solution was solvent exchanged from ethyl acetate into ethanol, creating a red slurry which was filtered to give the titled compound as a red solid in 79% yield.

EXAMPLE 8

Kinetic Study

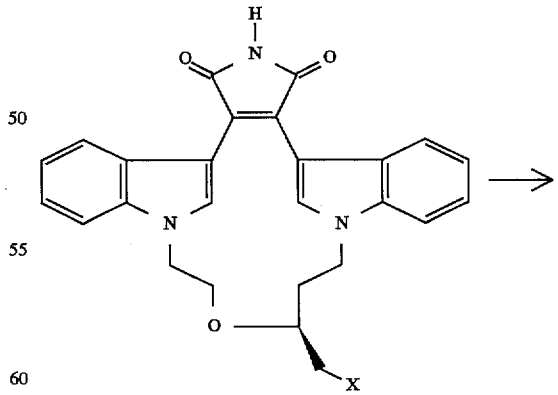

X = I (Compound A)
X = Br (Compound B)
X = Cl (Compound C)
X = OMs (Compound D)
X = OTs (Compound E)

-continued
Kinetic Study

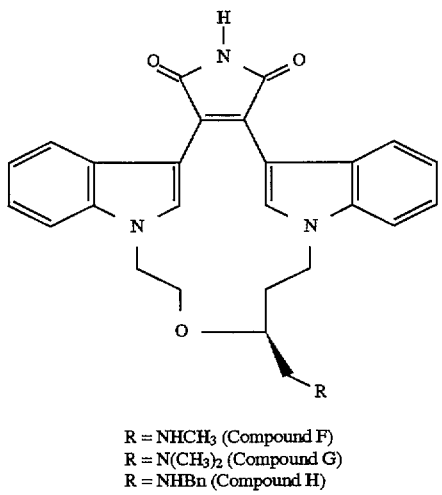

R = NHCH₃ (Compound F)
R = N(CH₃)₂ (Compound G)
R = NHBn (Compound H)

A 2 molar solution of dimethylamine in N,N-dimethylacetamide (DMA) was prepared for use in the kinetic studies. Compounds A (0.25 g, 0.45 mmol), B (0.229 g, 0.45 mmol), C (0.209 g, 0.45 mmol), D (0.236 g, 0.45 mmol), and E (0.271 g, 0.45 mmol) were each dissolved in DMA (~20 mL/g, 4–6 mL) and a 2 molar solution of dimethylamine in DMA (4.5 mL, 9.0 mmol, 20 eq.) was added to each reaction. The reaction solutions were capped, stirred at 23° C. and sampled for HPLC analysis over time. A 4.6 mm×25 cm Zorbax SB-CN column was utilized with an isocratic 50/50 THF/0.1% trifluroacetic acid buffered water mobile phase at 1 mL/min and a UV detector setting of 233 nm ($R_t$ Compound A=10.4 min., $R_t$ Compound B=9.3 min., $R_t$ Compound C=9.0 min., $R_t$ Compound D=6.2 min., $R_t$ Compound E=10.6 min.). Reaction concentrations were determined from a response factor which was obtained for each compound from the line equation of a three point calibration curve (concentrations of 0.1 mg/mL, 0.05 mg/mL and 0.025 mg/mL vs. corresponding response areas). Reaction samples (0.1 mL) were diluted to 25 mL in a volumetric flask before HPLC analysis, and the concentrations (mg/mL) were converted to molar concentrations (mmol/mL). The natural log of the dimethylamine concentration divided by the compound A, B, C, D, or E concentrations were plotted vs. time. The slope of the line obtained from each plot was divided by the difference of the initial amine concentration minus the initial compound concentrations to obtain the second order rate constants (units of $L M^{-1} Hr^{-1}$). The results are depicted in Table I.

EXAMPLE 9

Competitive Rate Studies of Mesylate vs. Bromide with Dimethylamine, Methylamine and Benzylamine A 2 molar solution of methyl amine and dimethylamine in N,N-dimethylacetamide (DMA) was prepared for use in the kinetic studies. Compounds D (1.03 g, 1.98 mmol) and B (1.00 g, 1.98 mmol) were combined in N,N-dimethylacetamide (20 mL/g for methylamine and dimethylamine reactions and 36 mL/g for benzylamine reaction) and a 2 molar solution of methylamine in DMA (19.8 mL, 39.7 mmol, 20 eq.) or a 2 molar solution of dimethylamine in DMA (19.8 mL, 39.7 mmol, 20 eq.) or benzylamine (4.25 g, 39.7 mmol, 20 eq) was added. The reaction solutions were capped, stirred at 23° C. and sampled for HPLC analysis over time. A 4.6 mm×25 cm Zorbax SB-CN column was utilized with an isocratic 45/55 THF/0.1% trifluroacetic acid buffered water mobile phase at 1 mL/min and a UV detector setting of 233 nm ($R_t$ Compound D=11.4 min., Rt Compound B=19.9 min.). Reaction concentrations were determined from a response factor which was obtained for compounds B and D from the line equation of a three point calibration curve (concentrations of 0.1 mg/mL, 0.05 mg/mL and 0.025 mg/mL vs. corresponding response areas). Reaction samples (0.1 mL) were diluted to 25 mL in a volumetric flask before HPLC analysis, and the concentrations (mg/mL) were converted to molar concentrations (mmol/mL). The natural log of the amine concentrations divided by the compound concentrations were plotted vs. time. The slope of the line obtained from each plot was divided by the difference of the initial amine concentration minus the initial compound concentrations to obtain the second order rate constants (units of $L M^{-1} Hr^{-1}$). The methylamino and benzylamino derivatives were prepared directly from the claimed bromide intermediate in high yield. The mesylate intermediate failed to produce the methylamino and benzylamino derivative directly in high yield.

As previously stated, the compounds of the present invention are additionally active as selective Protein Kinase C inhibitors. The activity of compounds were determined by the Calcium Calmodulin Dependent Protein Kinase Assay, Casein Protein Kinase II assay, cAMP-Dependent Protein Kinase Catalytic Subunit assay and the Protein-Tyrosine Kinase assay described in Heath et al., 08/413735, published as EP 0 657 458 Jun. 14, 1995, herein incorporated by reference. The claimed compounds are active and isozyme selective in the these assays having an $IC_{50}$ value of less than 10 µM.

Compounds with this demonstrated pharmacological activity are useful in the treatment of conditions in which protein kinase C has demonstrated a role in the pathology. Conditions recognized in the art include: diabetes mellitus and its complications (particularly microvascular diabetic complications, retinopathy, nephropathy, and neuropathy), ischemia, inflammation, central nervous system disorders, cardiovascular disease, Alzheimer's disease, dermatological disease and cancer.

The compounds of Formula II are preferably formulated prior to administration. Therefore, yet another embodiment of the present invention is a pharmaceutical formulation comprising a compound of Formula II and one or more pharmaceutically acceptable carriers, diluents or excipients.

The present pharmaceutical formulations are prepared by known procedures using well known and readily available ingredients. In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semisolid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosol (as a solid or in a liquid medium), soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyl and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient.

A pharmaceutically effective amount of the compound represents an amount capable of inhibiting PKC activity in mammals. A typical daily dose will contain from about 0.01 mg/kg to about 20 mg/kg of active compound. Preferred doses will be about 0.01 to about 10 mg/kg. The compositions are preferably formulated in a unit dosage form, each dosage containing from about 1 to about 500 mg, more usually about 5 to about 300 mg, of the active ingredient. However, it will be understood that the therapeutic dosage administered will be determined by the physician in the light of the relevant circumstances including the condition to be treated, the choice of compound to be administered and the chosen route of administration, and therefore the above dosage ranges are not intended to limit the scope of the invention in any way. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

The following formulation examples are illustrative only and are not intended to limit the scope of the invention in any way.

FORMULATION 1

Hard gelatin capsules are prepared using the following ingredients:

|  | Quantity (mg/capsule) |
|---|---|
| Active agent | 5 |
| starch, dried | 185 |
| magnesium stearate | 10 |
| Total | 200 mg |

The above ingredients are mixed and filled into hard gelatin capsules in 200 mg quantities.

FORMULATION 2

A tablet is prepared using the ingredients below:

|  | Quantity (mg/capsule) |
|---|---|
| Active agent | 20 |
| cellulose, microcrystalline | 400 |
| silicon dioxide, fumed | 10 |
| stearic acid | 5 |
| Total | 435 mg |

The components are blended and compressed to form tablets each weighing 435 mg.

FORMULATION 3

Tablets each containing 10 mg of active ingredient are made as follows:

|  | Quantity (mg/capsule) |
|---|---|
| Active agent | 10 mg |
| starch | 45 mg |
| microcrystalline cellulose | 35 mg |
| polyvinylpyrrolidone (as 10% solution in water) | 4 mg |
| sodium carboxymethyl starch | 4.5 mg |
| magnesium stearate | 0.5 mg |
| talc | 1 mg |
| Total | 100 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 100 mg.

FORMULATION 4

Capsules each containing 40 mg of medicament are made as follows:

|  | Quantity (mg/capsule) |
|---|---|
| Active agent | 40 mg |
| starch | 59 mg |
| microcrystalline cellulose | 59 mg |
| magnesium stearate | 2 mg |
| Total | 200 mg |

The active ingredient, cellulose, starch and magnesium stearate are blended, passed through a No. 45 mesh U.S. sieve, and filled into hard gelatin capsules in 200 mg quantities.

The principles, preferred embodiments and modes of operation of the present invention have been described in the foregoing specification. The invention which is intended to be protected herein, however, is not to be construed as limited to the particular forms disclosed, since they are to be regarded as illustrative rather than restrictive. Variations and changes may be made by those skilled in the art without departing from the spirit of the invention.

We claim:
1. A compound of the Formula:

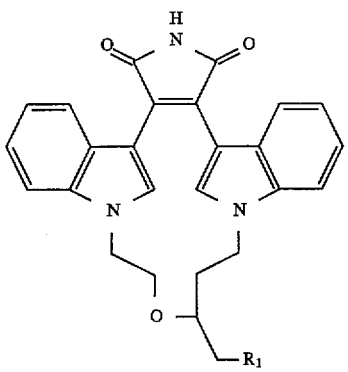

wherein $R_1$ is Br, I, or O-tosyl.

2. A compound of claim 1 of the Formula:

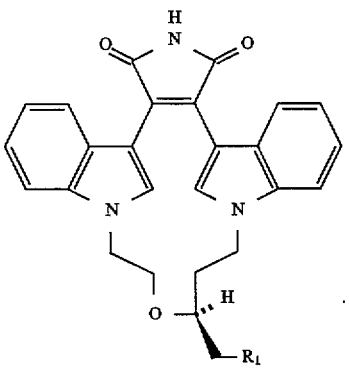

3. A compound of claim 1, wherein $R_1$ is Br or I.

4. A compound of claim 2, wherein $R_1$ is Br or I.

5. A pharmaceutical formulation comprising a compound of claim 1, and one or more pharmaceutically acceptable carriers, diluents or excipients.

6. A pharmaceutical formulation comprising a compound of claim 2, and one or more pharmaceutically acceptable carriers, diluents or excipients.

7. A pharmaceutical formulation comprising a compound of claim 3, and one or more pharmaceutically acceptable carriers, diluents or excipients.

8. A pharmaceutical formulation comprising a compound of claim 4, and one or more pharmaceutically acceptable carriers, diluents or excipients.

9. A process to prepare an amino substituted N,N'-bridged bisindolylmaleimide of the Formula:

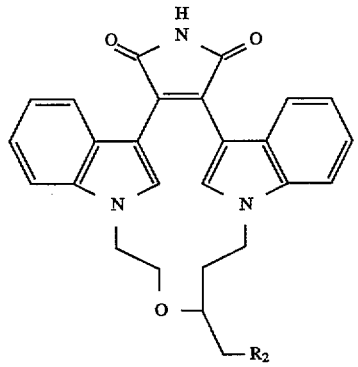

wherein $R_2$ is $-N(CF_3)CH_3$, $-NH(CF_3)$, or $-NR_3R_4$ wherein $R_3$ and $R_4$ are independently hydrogen, $C_1$-$C_4$ alkyl, phenyl, benzyl, or combine to the nitrogen to which they are bonded to form a saturated or unsaturated 5 or 6 member ring; which comprises reacting a compound of claim 1, with an amine in a non-reactive, polar solvent.

10. A process to prepare an amino substituted N,N'-bridged bisindolylmaleimide of the Formula:

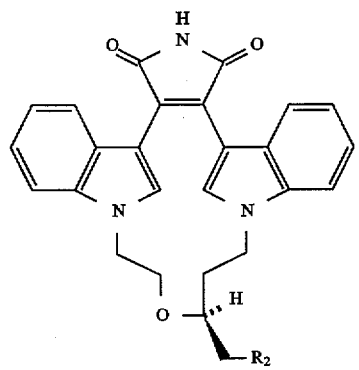

wherein $R_2$ is $-N(CF_3)CH_3$, $-NH(CF_3)$, or $-NR3R_4$ wherein $R_3$ and $R_4$ are independently hydrogen, $C_1$-$C_4$ alkyl, phenyl, benzyl, or combine to the nitrogen to which they are bonded to form a saturated or unsaturated 5 or 6 member ring; which comprises reacting a compound of claim 2, with an amine in a non-reactive, polar solvent.

11. A process of claim 10, wherein the compound of

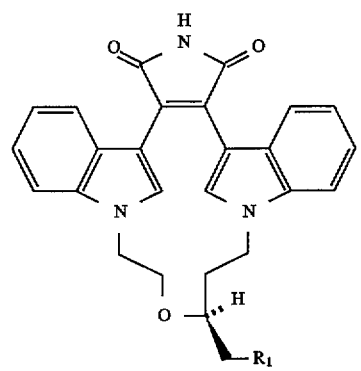

and $R_1$ is Br or I.

12. A process of claim 11, wherein the amine is $HN(CH_3)_2$ or $H_2N(CH_3)$.

13. A process of preparing a N,N'-bridged bisindolylmaleimide of the Formula (V):

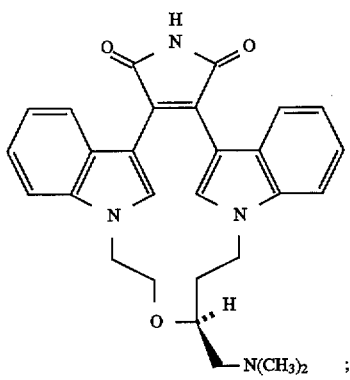

(V)

which comprises reacting a compound of formula:

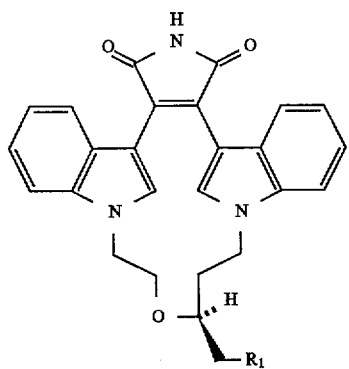

wherein $R_1$ is Br or I; with $HN(CH_3)_2$ in a non-reactive, polar solvent.

14. The process of preparing a compound of claim 1, which comprises converting a compound of the Formula:

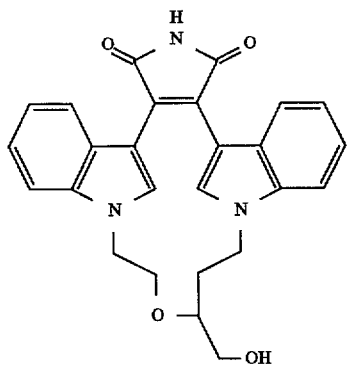

to a compound of claim 1.

15. The process of claim 14, wherein the process is carried out in the presence of $PX_3$, $(phenyl)_3PX_2$, or $(phenoxy)_3PX_2$ wherein X is bromo or iodo.

16. The process of claim 15, wherein the process is carried out in the presence of $(phenoxy)_3PBr_2$.

17. The process of preparing a compound of the Formula (V):

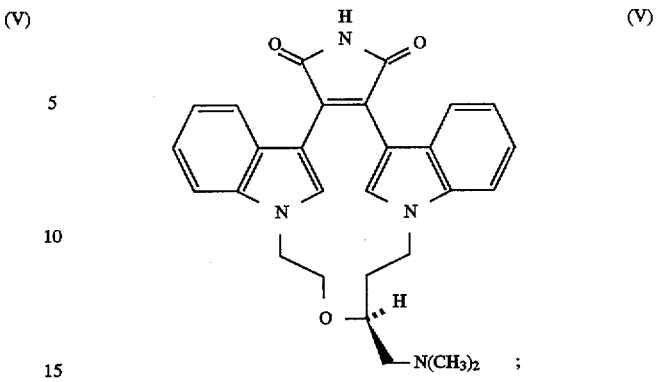

which comprises:

(a) Reacting a compound of the Formula (IIIa):

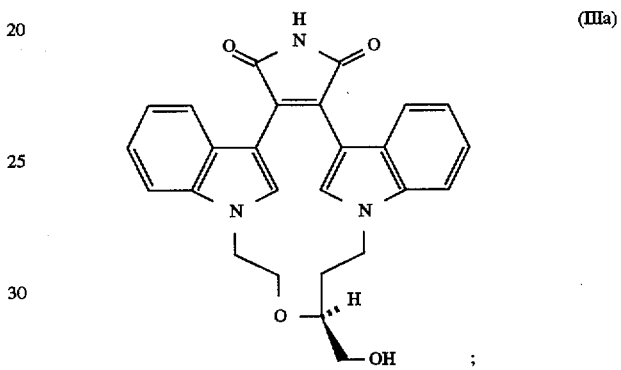

with $PX_3$, $(phenyl)_3PX_2$, or $(phenoxy)_3PX_2$ wherein X is bromo or iodo; to form a compound of the Formula (IIa):

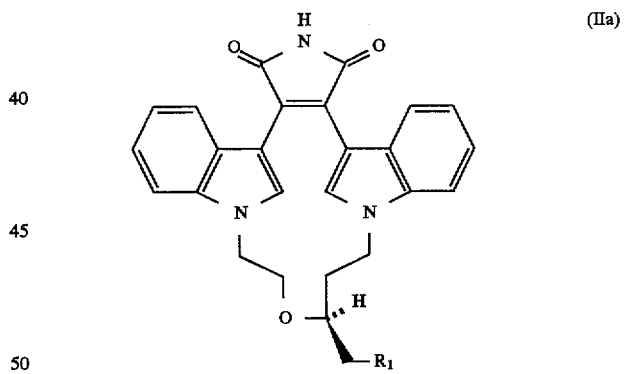

wherein $R_1$ is Br or I; and (b) Reacting a compound of formula (IIa) with $HN(CH_3)_2$ in a non-reactive, polar solvent.

18. The process of claim 17, wherein $R_1$ is Br.

19. The process of claim 18, which further comprises reacting the compound of Formula (V) with $CH_3SO_3H$.

* * * * *